United States Patent [19]

Minagawa et al.

[11] 4,105,629

[45] Aug. 8, 1978

[54] SYNTHETIC RESIN STABILIZER COMPRISING A THIOETHER ESTER AND HINDERED PHENOLIC CARBONATE

[75] Inventors: Motonobu Minagawa, Koshigaya; Yutaka Nakahara, Iwatsuki; Tohru Haruna, Okegawa, all of Japan

[73] Assignee: Argus Chemical Corporation, Brooklyn, N.Y.

[21] Appl. No.: 732,038

[22] Filed: Oct. 13, 1976

[30] Foreign Application Priority Data

Oct. 14, 1975 [JP] Japan .................. 50-123711

[51] Int. Cl.$^2$ ............... C08K 5/13; C08K 5/36
[52] U.S. Cl. ............ 260/45.8 NT; 260/45.85 S; 260/45.85 H; 260/45.95 BC; 260/45.95 R; 252/404; 252/406; 260/47 X A; 260/463; 528/196
[58] Field of Search ......... 260/45.85 S, 47 XA, 260/45.95 B, 45.95 R, 45.7 R, 860, 23 XA, 463, 45.8 NT; 252/404, 406

[56] References Cited

U.S. PATENT DOCUMENTS

| | | | |
|---|---|---|---|
| Re. 27,682 | 6/1973 | Schnell et al. ................. | 260/47 XA |
| 2,946,766 | 7/1960 | Schnell et al. ................. | 260/47 XA |
| 2,999,841 | 9/1961 | Csendes ........................ | 260/45.95 E |
| 3,026,264 | 3/1962 | Rocklin et al. ................ | 260/45.95 B |
| 3,036,036 | 5/1962 | Howe ............................. | 260/47 XA |
| 3,136,741 | 6/1964 | Schnell et al. ................. | 260/47 XA |
| 3,239,484 | 3/1966 | Stark ............................. | 260/45.95 B |
| 3,244,650 | 4/1966 | Hecker et al. ................. | 260/45.95 E |
| 3,272,869 | 9/1966 | O'Shea .......................... | 260/45.95 C |
| 3,274,258 | 9/1966 | Odenweller ................... | 260/45.95 C |
| 3,312,660 | 4/1967 | Kurkjy et al. .................. | 260/463 |
| 3,357,946 | 12/1967 | Burgess ......................... | 260/45.95 B |
| 3,420,894 | 1/1969 | Pierce et al. ................... | 260/47 XA |
| 3,453,225 | 7/1969 | Pollock .......................... | 260/23 XA |
| 3,510,507 | 5/1970 | Brown et al. ................... | 260/463 |
| 3,544,514 | 12/1970 | Schnell et al. ................. | 260/47 XA |
| 3,629,194 | 12/1971 | Onishi et al. ................... | 260/45.95 |
| 3,748,303 | 7/1973 | Becker et al. .................. | 260/47 XA |
| 3,758,549 | 9/1973 | Dexter ........................... | 260/398.5 |
| 4,009,148 | 2/1977 | Neuray et al. .................. | 260/463 |
| 4,032,510 | 6/1977 | Floyd et al. .................... | 260/45.85 |

FOREIGN PATENT DOCUMENTS 50-106,881  8/1975  Japan.

OTHER PUBLICATIONS

Polymer Engineering & Science, Jul. 1966, pp. 231–239 – article by Gordon et al.

*Primary Examiner*—V. P. Hoke
*Attorney, Agent, or Firm*—Otto S. Kauder

[57] ABSTRACT

Stabilizer compositions are provided whose ingredients interact synergistically to improve the resistance to deterioration on heating of synthetic resin compositions. The interacting ingredients are (a) a thioether carboxylic acid ester of a polyhydric alcohol having 5 to 15 carbon atoms and 3 to 8 primary hydroxyl groups with a 3-alkylthiopropionic acid having 4 to about 34 carbon atoms, and (b) at least one carbonate ester of an ortho-substituted polyhydric phenol having in the molecule one to three benzenoid rings, two to three phenolic hydroxyl groups, and in each benzenoid ring one to two alkyl, cycloalkyl, or aralkyl groups of which at least one is positioned ortho to a phenolic hydroxyl group.

Synthetic resin compositions are provided that are stabilized with the stabilizer compositions disclosed, including olefin polymers, polyamides, acrylic polymers, and vinyl halide polymers.

18 Claims, No Drawings

SYNTHETIC RESIN STABILIZER COMPRISING A THIOETHER ESTER AND HINDERED PHENOLIC CARBONATE

BACKGROUND OF THE INVENTION

This invention relates to new stabilizer combinations, and to synthetic resin compositions, particularly olefin polymer, acrylic polymer, vinyl halide polymer, and polyamide compositions containing the same, and having as a result an increased resistance to deterioration in color and mechanical properties when heated at elevated temperatures of the order of 150° C and higher.

The pioneer disclosure of thioether carboxylic acid esters for stabilizing a polymer is believed to be by M. Gribbins in U.S. Pat. No. 2,519,755 of Aug. 22, 1950. Gribbins stabilized ethylene polymers with 0.001% to 5% by weight of a beta-thioether of an ester of propionic acid having the formula

ROOCCH$_2$CH$_2$S—X, in which R is an alkyl or a cycloalkyl radical such as n- and isobutyl, amyl, heptyl, nonyl, decyl, lauryl, glycyl, cinnamyl, capryl, benzyl, allyl, cetyl, stearyl, palmityl, cyclohexyl, and similar groups, and X is:

1. a hydrocarbon group such as, e.g., the alkyl groups: methyl, ethyl, propyl, butyl, lauryl; the aryl groups: phenyl, naphthyl, benzyl; and such groups as p-methoxy phenyl, p-hydroxyphenyl and cyclohexyl.
2. an oxygenated-hydrocarbon group such as, e.g., the alcohol groups: hydroxymethylene, hydroxyethylene, and hydroxybutylene; the ether groups: methoxymethylene, methoxyethylene and ethoxyethylene; and acid groups and the R esters thereof: carboxymethylene, carboxyethylene, carboxypropylene and carboxybutylene; and aldehyde radicals as aldehydoethyl.
3. a sulfur-hydrocarbon group such as, e.g., mercaptoethyl, mercaptopropyl, mercaptobutyl, mercaptoisobutyl, mercaptohexyl and ethiaethyl.
4. a sulfur-and oxygenated-hydrocarbon group such as, e.g., carboxyethiaethyl (CH$_2$CH$_2$SCH$_2$CH$_2$COOH)$_2$ carboxyethiaethyldithiaethyl (CH$_2$CH$_2$SSCH$_2$CH$_2$SCH$_2$CH$_2$COOH), carboxyethiaisobutyl (CH$_2$CH$_2$CH(CH$_3$)SCH$_2$CH$_2$COOH) and carboxyethiapropyl (CH$_2$CH$_2$CH$_2$SCH$_2$CH$_2$COOH).
5. a sulfur-and nitrogen-containing hydrocarbon group such as, e.g., 3-benzothiazyl mercaptopropionic acid, specifically described in U.S. Pat. No. 2,397,960.

Among these, Gribbins found the di-higher alkyl beta-thiodipropionates and especially the dilauryl and distearyl esters outstanding. Subsequently, thioether carboxylic acid esters and in particular thiodipropionates have been employed in conjunction with other stabilizers such as a polyhydric phenol in the stabilization of polypropylene and other polyolefins against degradation upon heating or ageing under atmosphere conditions. Disclosures by C. Tholstrup, U.S. Pat Nos. 3,033,814 of May 8, 1962 and 3,160,680 of Dec. 8, 1964; L. Rayner, U.S. Pat. No. 3,181,971 of May 4, 1965; D. Bown, U.S. Pat. No. 3,242,135 of Mar. 22, 1966; S. Murdock, U.S. Pat. No. 3,245,949 of April 12, 1966; H. Hagemeyer, U.S. Pat. No. 3,282,890 of Nov. 1, 1966; J. Casey, U.S. Pat. No. 3,496,128 of Feb. 17, 1970 and 3,586,657 of June 22, 1971; M. Minagawa, U.S. Pat. No. 3,549,572 of Dec. 22, 1970, 3,629,189 of Dec. 21, 1971, 3,673,152 of June 27, 1972, U.S. Pat. No. 3,849,370 of Nov. 19, 1974 and 3,869,423 of Mar. 4, 1975; W. Drake U.S. Pat. No. 3,624,026 of Nov. 30, 1971; A. DiBattista, U.S. Pat. No. 3,824,192 of July 16, 1974; B. Cook, U.S. Pat. No. 3,850,877 and H. Mueller U.S. Pat. No. 3,850,918 of Nov. 26, 1974; M. Dexter U.S. Pat. No. 3,856,748 of Dec. 24, 1974, 3,888,824 of June 10, 1975, and 3,903,160 of Sept. 2, 1975; P. Klemchuk U.S. Pat. No. 3,860,558 of Jan. 14, 1975; M. Rasberger U.S. Pat. No. 3,867,340 of Feb. 18, and 3,901,931 of Aug. 26, 1975; H. Brunetti U.S. Pat. Nos. 3,867,337 of Feb. 18 and 3,873,498 of Mar. 25, 1975; S. Rosenberger U.S. Pat. Nos. 3,884,874 of May 20 and 3,887,518 of June 3, 1975; C. Ramey U.S. Pat. No. 3,907,803 of Sept. 23, 1975 are representative of a very large number of stabilizer combinations including dilauryl and distearyl thiodipropionate or other dialkyl thiodipropionates along with polyhydricphenols and sometimes organic phosphites, metallic stearates, ultraviolet absorbers, nickel compounds, and heavy metal deactivators for use in polypropylene and other polyolefins.

Thiodipropionate esters are also used in stabilizer combinations for other polymers such as elastomeric glycol-terephthalic acid polyesters disclosed by A. Bell in U.S. Pat. No. 3,157,619 of Nov. 17, 1964; high molecular weight polymers of formaldehyde disclosed by R. Green in U.S. Pat. No. 3,228,885 of Nov. 29, 1966, organot in compound stabilized polyvinyl chloride disclosed by O. Kauder in U.S. Pat. No. 3,297,629 of Jan. 10, 1967 and C. Stapfer in U.S. Pat. No. 3,890,276 of June 17, 1975; acrylonitrile-butadiene-styrene (ABS) polymers disclosed by W. Cummings U.S. Pat. No. 3,267,069 of Aug. 16, 1966; A. Hecker U.S. Pat. No. 3,472,813 of Oct. 14, 1969 and P. Marinacci U.S. Pat. No. 3,637,555; and polyamides disclosed by T. White in U.S. Pat. No. 3,904,705 of Sept. 9, 1975. The polyhydric phenol is believed to function as an antioxidant in such combinations, and the thiodipropionate ester is often termed a costabilizer, Secondary stabilizer, synergist, or decomposer of organic peroxides.

While dialkylthiodipropionates have many favorable attributes such as availability in high purity at reasonable cost, a low degree of toxicity, and generally good stabilizing effectiveness, certain problems attendant on their use have long been recognized, particularly the need to use high concentrations in certain highly stressed formulations to obtain the required heat stability, and a tendency to lose effectiveness in use as a result of exposure to the leaching action of moving streams of warm water and warm air as in the washing and drying cycles of automatic dishwashers and laundry machines.

Attempts to improve on these characteristics have included the use of more efficient and more permanent thiodipropionate esters as well as more effective antioxidants and stabilizer combinations. Thus A. Hecker in U.S. Pat. No. 3,244,650 of Apr. 5, 1966 disclosed a stabilizer system for polypropylene composed of three stabilizers: an organic polyhydric phenol, an organic phosphite and a polyvalent metal salt of an organic acid. To this sytem, U.S. Pat. No. 3,255,136 of June 7, 1966 added a fourth ingredient, a thiodipropionic acid ester having the formula:

R$_1$OOCCH$_2$—S—CH$_2$CH$_2$COOY in which R$_1$ is an organic radical selected from the group consisting of hydrocarbon radicals such as alkyl, alkenyl, aryl, cycloalkyl and mixed alkyl aryl and mixed alkyl cycloalkyl radicals; hydroxyalkyl and hydroxyalkyloxyalkylene radicals; and esters thereof with aliphatic carboxylic acids; and Y is selected from the group consisting of (a) hydrogen, (b) a second R radical $R_2$, which can be the same as or different from the $R_1$ radical, (c) a polymeric chain of n thiodipropionic acid ester units:

where Z is hydrogen, $R_2$ or M, n is the number of thiodipropionic acid ester units in the chain, and X is a bivalent hydrocarbon group of the type of $R_1$, that is alkylene, alkenylene, cycloalkylene, mixed alkylene-arylene and mixed alkylene-cycloalkylene radicals: hydroxyalkylene and hydroxyalkyloxyalkylene radicals; and esters thereof with aliphatic carboxylic acids; and (d) a polyvalent metal M of Group II of the periodic table such as zinc, calcium, cadmium, barium, magnesium and strontium.

The molecular weights of the R and Y radicals are taken such that with the remainder of the molecule the thiodipropionic ester has a total of from about ten to about sixty atoms per sulfur atom.

U.S. Pat. No. 3,378,516, patented Apr. 16, 1968 to Tholstrup, Bell and Kibler, proposes combinations including linear thiodi alkanoate polyesters obtained from a thiodialkanoic acid and a diol having a molecular weight of from about 500 to 4000, together with a phenolic antioxidant and/or a phosphite. These combinations are said to display synergistic stabilizing effectiveness.

H. Schirmer in U.S. Pat. No. 3,598,776 of Aug. 10, 1971, disclosed that the incorporation of 10% by weight disproportionated resin in polypropylene enabled him to use 2% by weight dilaurylthiodipropionate (LTP) in the polymer without blooming while in the absence of the rosin only 1% could be used without blooming and the stability of the polymer with the rosin that the higher LTP concentration was significantly increased.

H. Schutze in U.S. Pat. No. 3,630,991 of Dec. 28, 1971 disclosed non-exuding and non-volatile sulfur containing esters of cyclic terpene alcohols for the stabilization of 2 to 8 carbon alpha-olefin polymers together with hindered phenols. Schutze's esters may be represented by the structural formulae

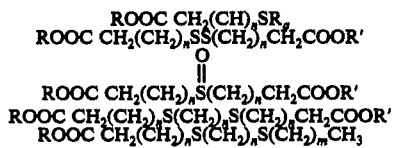

where
$R_a$ is — $CH_2(CH_2)_nCOOR'$ or alkyl
$n = 1$ to 5
$m = 1$ to 16
R is a radical selected from the group consisting of abietyl, hydroabietyl, tetrahydroabietyl, dihydroabietyl, dehydroabietyl, dihydropimaryl, tetrahydropimaryl, borneyl, alpha-terpineyl, B-terpineyl, V-terpineyl, methyl, and dihydroterpineyl, and R' is a radical selected from the group consisting of abietyl, hydroabietyl, tetrahydroabietyl, dihydroabietyl, dehydroabietyl, dihydropimaryl, tetrahydropimaryl, borneyl, alpha-terpineyl, B-terpineyl, methyl, and dihydroterpineyl.

A. Onishi, in U.S. Pat. No. 3,629,194 of December 21, 1971 disclosed a polyolefin resin stabilized against thermal aging with esters of alkyl thiopropionic or alkyl thiobutyric acid with a polyol having up to five hydroxyl groups, in combination (optionally) with a phenolic antioxidant. The alkyl thiopropionic or alkyl thiobutyric acid esters are defined as having one of the formulae:

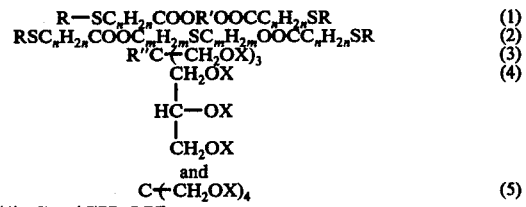

and (5) C—$(CH_2OX)_4$
wherein
R is an alkyl of 8 to 30 carbon atoms,
m and n are each integers of 2 or 3,
R' is an alkylene containing 2 to 12 carbon atoms, R" is an alkyl containing 1 to 20 carbon atoms,
X is hydrogen or —OC—$C_nH_{2n}$SR, at least one of which is —OCC$_n$H$_{2n}$SR,
the $R_1$, R' and R" moieties in one compound being the same or different.

The phenolic antioxidants are defined by Onishi as mono-or polyhydric phenolic compounds in which at least one of the ortho positions to a hydroxyl group is substituted by an alkyl, aralkyl, or cycloalkyl group. The substituents preferably contain carbon atoms of a number of the order of 3 to 10, and the alkyl group, inclusive of that in an aralkyl and cycloalkyl groups can be unsaturated. The phenolic compounds may be further substituted, and the phenolic compounds may be polyphenolic such as bisphenolic, trisphenolic, or tetrakisphenolic compounds in which phenolic nuclei are connected by a connecting group such as an alkylene, a thioether, or a triazinoxyl group.

M. Dexter in U.S. Pat. No. 3,758,549 of Sept. 11, 1973 disclosed alkyl esters derived from alkyl thioalkanoic acids and alkane polyols, such as pentaerythritol tetrakis, 3-n-dodecylthiopropionate, and ethylene-bis-3-n-dodecylthiopropionate. These are used in combination with phenolic antioxidants to effectively stabilize polyolefins from the deleterious effects of heat and oxygen. The alkyl esters are defined by the formula:

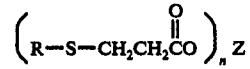

wherein
R is an alkyl group of from one to eighteen carbons atoms,
n has a value of from 2 to 4; and
Z is an aliphatic hydrocarbon of the formula:

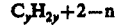

in which y has a value of from 2 to 18 when n is 2 and value of from 3 to 6 when n is greater than 2, the value of y in all cases being equal to or greater than that of n.

M. Minagawa in Japanese Kokai 75/106881 of Aug. 27, 1975 disclosed stabilized resin compositions containing 3-alkylthiopropionate esters of alcohols containing a nitrogen-heterocyclic ring, for example tris(2-hydroxyethyl isocyanurate) and optionally a phenolic antioxidant.

E. Schurdak in U.S. Pat. No. 3,966,675 of June 29, 1976 has disclosed mixtures of pentaerythritol tetrakis (3-n-dodecylthiopropionate) with bis(4-t-butyl-3-hydroxy-2,6-dimethylbenzyl) dithiolterepthalate or 1,3,5-tris(4-t-butyl-3-hydroxy-2,6-dimethylbenzyl)-s-triazine-2,4,6-trione that are stated to be extremely effective in inhibiting the thermal degradation of polypropylene.

There have also been disclosures of improved stabilization of olefin polymers, vinyl chloride polymers, and other synthetic resins with thiodipropionate esters used together with special phenolic phosphites. Thus, D. Bown, U.S. Pat. No. 3,297,631 of Jan. 10, 1967 disclosed condensation products of phosphorus compounds with bisphenols and trisphenols which may be represented by the structures:

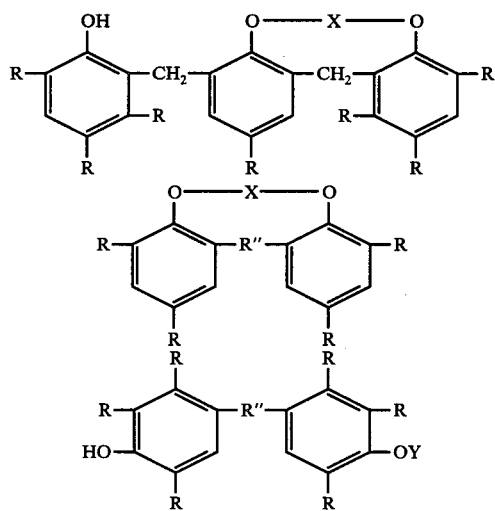

Where:

X is selected from the following: >P—OR'; >P—R';

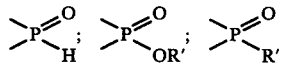

and Y is selected from the following: —P(OR')$_2$;

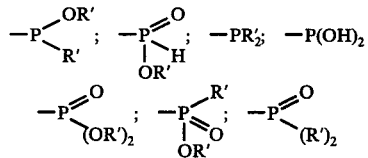

R is hydrogen, alkyl of 1 to 16 carbon atoms or aryl or a combination of these; R' is alkyl of 1 to 16 carbon atoms or aryl, and R" is alkylidene of 1 to 16 carbon atoms or an aryl-substituted alkylidene.

C. Baranauckas, U.S. Pat. No. 3,305,608 of Feb. 21, 1967, disclosed phenolic phosphites useful as polymer stabilizers prepared by reacting a triorganophosphite, a polyol, and an aromatic material having two to six phenolic hydroxyl groups at 60°–180° C in specified proportions.

G. Brindell, U.S. Pat. No. 3,412,064 of Nov. 19, 1968 disclosed phenolic phosphites represented by the general formula:

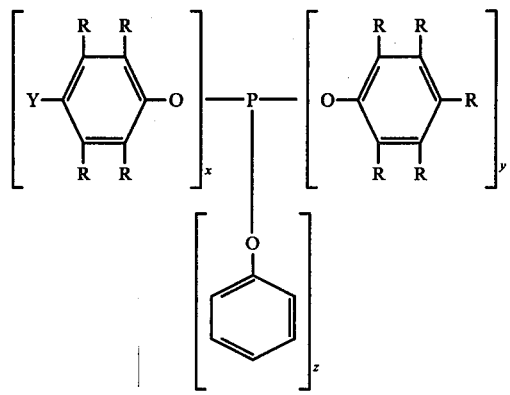

where $x$ is from 1 to 3, $y$ and $z$ each from 0 to 2, $x+y+z=3$, R is hydrogen or alkyl and Y is hydroxyl or a roup of the formula

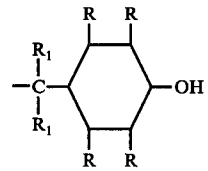

where R is hydrogen or alkyl

M. Larrison, U.S. Pat. No. 3,419,524 of Dec. 31, 1968, disclosed phosphites useful as polymer stabilizers having the formula:

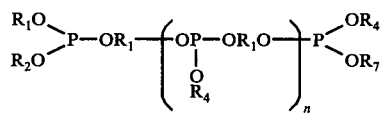

where $R_1$, $R_2$, $R_4$, $R_6$, and $R_7$ are aryl or haloaryl, and $R_3$ and $R_5$ are a polyalkylidene glycol or an alkylidene bisphenol or a hydrogenated alkylidene bisphenol or a ring halogenated alkylidene bisphenol from which the two terminal hydrogens have been removed.

O. Kauder et al, U.S. Pat. Nos. 3,476,699 of Nov. 4, 1969 and 3,655,832 of Apr. 11, 1972 disclosed organic phsophites containing a free phenolic hydroxyl group and defined by the formula:

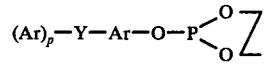

wherein Z is selected from the group consisting of hydrogen and aliphatic, cycloaliphatic, aromatic, heterocyclic and (Ar)$_p$— Y-Ar groups, taken in sufficient number to satisfy the valences of the two phosphite oxygen atoms; Y is a polyvalent linking group selected from the group consisting of oxygen; aliphatic, cycloaliphatic and aromatic hydrocarbon groups attached to each Ar group through a carbon atom not a member of an aromatic ring; oxyaliphatic; thioaliphatic, oxycycloaliphatic, thiocycloaliphatic; heterocyclic; oxyheterocyclic, thioheterocyclic, carbonyl, sulfinyl; and sulfonyl groups; Ar is a phenolic nucleus which can be phenyl or a polycarbocyclic group having condensed or separate phenyl rings; each Ar group is either connected through an oxygen atom to a phosphite group or contains a free phenolic hydroxyl group, or both; and p is a number, one or greater, and preferably from one to four, which defines the number of Ar groups linked to Y.

L. Firedman, U.S. Pat. No. 3,516,963 of June 23, 1970, disclosed phosphites having the formula:

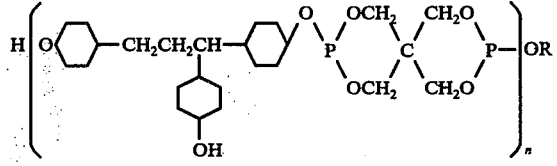

where R is alkyl, alkenyl, aryl, aralkyl, haloaryl, haloalkyl
or

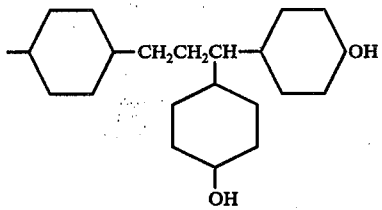

and $n$ is an integer of at least 1. $n$ can be 2, 3, 4, 5, 6, 7, 8, 10, 50, 100 or even more.

D. Brown et al. in U.S. Pat. Nos. 3,510,507 of May 5, 1970 and 3,691,132 of Sept. 12, 1972 disclosed polyolefins stabilized with polyphosphites, polyphosphates, polyphosphonites, polyphosphonates, polyborates, polycarbonates, and polysilanes which are condensation products of a 4,4'-bisphenol with a condensing or linking agent which may be of the ester type, such as the esters of triaryl or mixed aryl-alkyl compounds, or the acid halide type. Bown's condensation product stabilizers have molecular weights between 600 and 8000 or higher and are described by the structural formula,

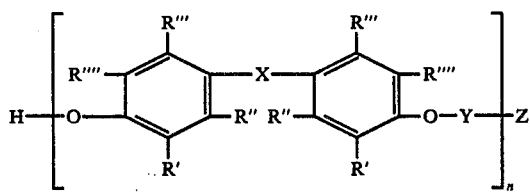

where X is selected from the group consisting of

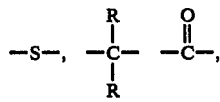

—C—C, and C—A—C— where A is a $C_1$ to $C_{16}$ alkylene or an arylene; R', R", R''', and R'''' are selected from the group consisting of hydrogen, $C_1$ to $C_{18}$ alkyls, and an aryl group; Y is selected from the group of

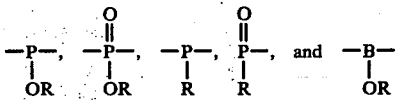

where R is hydrogen, a $C_1$ to $C_{18}$ alkyl, or aryl;

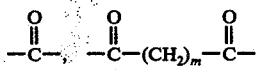

where $m$ is 0 to 10, preferably 4 to 8,

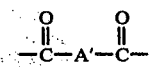

where A' is $(CH_2)_n$—S—$(CH_2)_n$ or —$(CH_2)_n$—S—$(CH_2)_m$—S—$(CH_2)_n$ where $n$ is 0 to 10, preferably 2 and $m$ is 0 to 10, preferably 5;

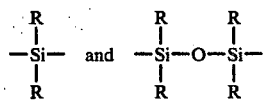

where R is an alkyl, preferably methyl, and Z is

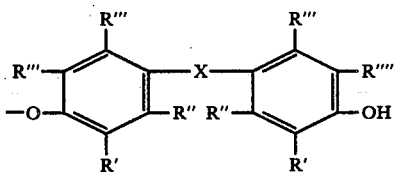

where R', R", R''', R'''', and X correspond respectively to the R', R", R''', R'''', and X previously selected when $n$ has a value from 1 to 15 or Z may be derived from the compound used to introduce Y into the product when $n$ has a value from 2 to 15, for example —R or —OR where R is hydrogen, an alkyl, or aryl. When Y in the formula of Brown's stabilizer is

the stabilizer is a type of hydroxyaryl phosphite. Similarly, when Y in the formula is

the stabilizer is a hydroxyaryl carbonate.

Bown's condensation products are described as especially effective in high molecular weight solid polyolefins when used together with a dialkyl sulfide costabilizer such as dilauryl thiodipropionate, distearyl thiodipropionate, ditridecyl thiodipropionate, dicetyl sulfide, bis(tetradecylmercapto) paraxylylene, and 10,24-dithiotetracontane.

J. Floyd et al in German published application 2505071 of August 14, 1975 abstracted in Chemical Abstracts 1976, Volume 84, abstract no. 5945f, disclosed low molecular weight polycarbonate esters of bisphenols such as 2,2-bis(3-t-butyl-4-hydroxyphenylpropane)

and 4,4'-butylidene bis (6-t-butyl-3-methylphenol) prepared in such a was as to contain few or no free phenolic hydroxyl groups as being highly effective heat and light stabilizers for polyolefins and giving a synergistic effect with distearyl thiodipropionate, tris (nonylphenyl) phosphite, and distearyl pentaerythritoldiphosphite.

SUMMARY OF THE INVENTION

In accordance with this invention, the resistance to deterioration upon heating of synthetic resin is increased synergistically by compounding the resin with a stabilizer composition comprising in combination (a) at least one thioether ester of a polyhydric alcohol having 5 to 15 carbon atoms and 3 to 8 primary hydroxyl groups with a 3-alkylthiopropionic acid having 4 to about 34 carbon atoms, and (b) at least one carbonate ester of an ortho-substituted polyhydric phenol having in the molecule one to three benzenoid rings, two to three phenolic hydroxyl groups, and in each benzenoid ring one to two alkyl, aryl, cycloalkyl, aralkyl or alkaryl groups of which at least one is positioned ortho to a phenolic hydroxyl group. Quite small amounts of the stabilizer composition are effective in increasing resistance to deterioration. The amount of each ingredient of the stabilizer composition required can be as little as 0.001% by weight of the resin and up to about 5% by weight; larger amounts can be used but tend to be unnecessary and wasteful. The amount of stabilizer composition to be used ranges from 0.002% to about 10% by weight of the resin, preferably from 0.03% to 5% by weight. The weight ratio of the polyhydric alcohol thioether carboxylic acid ester to the carbonate ester in the stabilizer composition of this invention can range from about 20 to 1 to about 1 to 2.

In addition to increasing the resistance to deterioration on heating, the stabilizer compositions of this invention impart to resin compositions in which they are used outstanding resistance to the deleterious effects of ultraviolet light and excellent resistance to the impairment of physical properites resulting from the leaching of stabilizers by aqueous solutions in contact with the stabilizing resin compositions.

DESCRIPTION OF THE PREFERRED EMBODIMENTS

The thioether carboxylic acid ester of a polyhydric alcohol ingredient (a) of the stabilizer composition of this invention is derived from a polyhydric alcohol having 5 to 15 carbon atoms and 3 to 8 primary hydroxyl groups by esterification with at least one molar proportion of a 3-alkylthiopropionic acid. The polyhydric alcohol can contain inert substituents such as ether groups, thioether groups, amide groups, and amine groups, can can be open-chain or cyclic. Useful and economically available polyhydric alcohols that can be used in the form of their 3-alkylthiopropionic acid esters include triethanolamine, 1,2,3-tris (2-hydroxyethyl)propane, 1,3,5-tris(2-hydroxyethyl)isocyanurate, trimethylolpropane, trimethylolethane, 2,2,2',2'-tetrakis (hydroxymethyl)dibutyl ether, pentaerythritol, dipentaerythritol, tripentaerythritol, and 2,2-dimethylpropanediolbis(dimethylolpropionate). The 3-alkylthiopropionic acid has 4 to about 34 carbon atoms, of which 3 to 4 are taken up in the propionic acid group which is either unsubstituted or carries a single methyl substituent, and the remaining 1 to about 30 make up the 3-alkyl group attached to sulfur. Alkyl groups attached to sulfur can be for example methyl, ethyl, n-propyl, isopropyl, n-butyl, isobutyl, sec-butyl, t-butyl, isoamyl, t-amyl, hexyl, heptyl, n-octyl, t-octyl, 2-ethylhexyl, nonyl, n-decyl, isodecyl, n-decyl, t-dodecyl, isotridecyl, n-tetradecyl, 2-butyl-octyl, n-hexadecyl, n-octadecyl, eicosanyl, tetracosanyl, octacosanyl and triacontanyl. Of these, alkyl groups attached to sulfur through a -CH$_2$- group, that is so-called primary alkyl groups, are preferred.

A preferred group of polyhydric alcohol thioether carboxylic esters of this invention is defined by the formual

in which Z is a residue of a polyhydric alcohol, $R_3$ is selected from the group consisting of methyl and hydrogen, $R_4$ is a primary alkyl group having 1 to about 30 carbon atoms, $p$ is an integer from 3 to 8, and $q$ is an integer from zero to p-1.

Among polyhydric alcohol thioether carboxylic esters that can be used in the stabilizer composition of this invention there can be mentioned pentaerythritol di(3-methylthiopropionate), trimethylolethanetris(3-ethylthio2-methylpropionate), dipentaerythritol hexakis (3-isotridecylthiopropionate) 1,2,3-tris(3-butylthiopropionyloxyethoxy)propane, 2,2,2', 2'-tetrakis(3-n-octylthio2-methylpropionyloxymethyl)dibutyl ether, N,N', N'', N'''-tetrakis (3-n-dodecylthiopropionyloxethyl)glycoluril, 1,3,5-tris(3-n-tetradecylthiopropionyloxyethyl)isocyanurate, pentaerythritol tetrakis(3-n-pentylthiopropionate), trimethylolpropane 3-n-dodecylthio-2-methylpropionate, triethanolamine triester of 3-eicosanylthiopropionic acid, tripentaerythritol octakis (3-methyl-thio-2-methylpropionate) and tetrakis (2,2-dimethylpropanediolbis) dimethylolpropionate 3-hexadecylthiopropionic acid tetraester. These and related thioether carboxylic esters are known compounds or homologs of known compounds that can be prepared by standard methods, such as the esterifications of the desired polyhydric alcohol with the 3-alkylthiopropionic acid, suitably in presence of an esterification catalyst and an azeotroping solvent to assist in removing reaction water, or alternatively the transesterification of a lower alkyl ester of the 3-alkylthiopropionic acid with the polyhydric alcohol with removal of the lower alkanol being displaced. Useful preparative techniques are disclosed, for example, by M. Dexter in U.S. Pat. No. 3,758,549 and M. Minagawa in Japanese Kokai 75/106881.

The carbonate ester is a carbonate of a dihydric or trihydric phenol characterized by certain essential structural features necessary for the synergistically enhanced stabilizing effectiveness in the stabilizer composition of this invention. These features are a controlled molecular weight in a range such that the carbonate ester is low in volatility and still sufficiently mobile in the polymer being stabilized for optimum effectiveness, which corresponds to a molecular weight range from 400 to about 4000; and in each benzenoid ring of the esterified dihydric or trihydric phenol one to two alkyl, cycloalkyl, or aralkyl groups having 1 to 10 carbon atoms of which at least one is positioned ortho to a phenolic hydroxyl group which can be a free hydroxyl or a carbonate ester. These recited features are critical to the observed effectiveness and in their absence the desired effectiveness in the stabilizer composition with the thioether ester according to this invention is not obtained. For reasons that are not well understood the greatest stabilizing effectiveness in the composition of this invention is associated with carbonate esters having an odd number of benzenoid rings in the dihydric or trihydric phenol.

A preferred class of carbonate ester components of the stabilizer composition of this invention is derived from ortho-substituted 1,3- and 1,4- dihydric phenols having one benzenoid ring such as 2,5-di-t-butylhydroquinone, 2,36-trimethylhydroquinone, 2-methylresorcinol, and 2,6-di-t-butylresorcinol.

Also useful carbonate ester compounds of the stabilizer composition are carbonate esters of ortho-substituted bisphenols having two ortho-substituted phenol groups linked directly or through a two valent hydrocarbon group such as 2,2'-methylene bis(4-methyl-6-t-butyl-phenol), 2,2'-methylene bis (4-ethyl-6-t-butylphenol), 2,2'-methylene bis (4-methyl-6-(1-methylcyclohexyl) phenol), 2,2'-n-butylidene bis(4,6-dimethylphenol), bis-1,1-(2'-hydroxy-3'5'-dimethylphenyl)-3,5,5-trimethylhexane, 2,2'-cyclohexylidene bis (4-ethyl-6-t-butylphenol), 2,2'-isopropylbenzylidene bis (4-ethyl-6-t-butylphenol), 4,4'-bis(2,6-di-t-butylphenol), 4, 4'-methylene bis(2-methyl-6-t-butylphenol), 4,4'-methylene bis(2,6-di-t-butylphenol), 4,4'-isopropylidene bis (2-phenylethylphenol), 4,4'-n-butylidene bis (3-methyl-6-t-butylphenol, 4,4'-cyclohexylidene bis(2-t-butylphenol), 4,4'-cyclohexylidene bis(2-cyclohexylphenol), and 4,4'-benzylidene bis(2-t-butyl-5-methylphenol).

Another preferred class of carbonate esters than can be used in the composition of this invention is the class of carbonate esters of ortho-substituted bisphenols having two ortho-substituted phenolic groups linked through oxygen or sulfur, such as 4,4'-oxobis(3-methyl-6-isopropylphenol), 4,4'-thiobis(2-methyl-6-t-butylphenol), 4,4'-thiobis (3-methyl-6-t-butylphenol), 4,4'-sulfobis (3-methyl-6-t-butylphenol, bis(2-methyl-4-hydroxy-5-t-butylbenzyl) sulfide, bis(3,5-di-t-butyl-4-hydroxy benzyl) sulfide, 2,2'-thiobis(4-t-butyl-6-methyl-phenol), 2,2'-thiobis(4-methyl-6-t-butyl-phenol), and 2,2'-thiobis(4,6-di-t-butylphenol).

A particularly preferred class of carbonate ester components of the stabilizer composition is the class of carbonate esters of ortho-substituted trisphenols having three ortho-substituted phenolic groups, such as 1,1,3-tris(2'-methyl-4'-hydroxy-5'-t-butylphenyl) butane, 1,3,5-tris(3',5'-di-t-butyl-4'-hydroxybenzyl)-2,4,6-trimethylbenzene, 2,2-bis(3'-t-butyl-4'-hydroxyphenyl)-4-(3",5"-di-t-butyl-4"-hydroxyphenyl)butane, and 2,2-bis(2'-methyl-5'-t-butyl-4'-hydroxyphenyl)-4-(3",5"-di-t-butyl-4"-hydroxyphenyl)butane.

The most preferred group of carbonate esters used in stabilizer compositions of this invention is defined by the formula

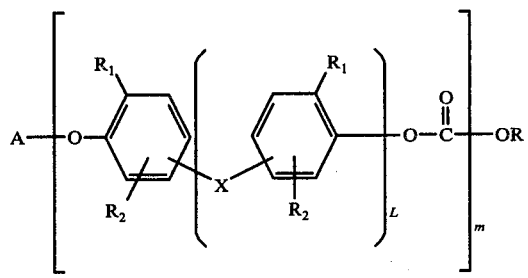

in which independently at each occurrence $R_1$ is selected from the group consisting of alkyl, cycloalkyl or arylalkyl radicals, $R_2$ is selected from the group consisting of hydrogen and $R_1$. and A is selected from the group consisting of hydrogen and

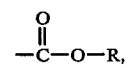

R is selected from the group consisting of alkyl, aryl, alkaryl, aralkyl, cycloakyl and

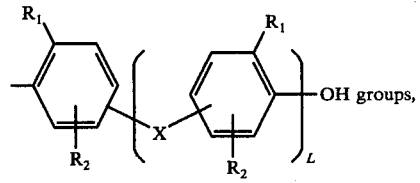

X is selected from the group consisting of —S—,

—CH$_2$SCH$_2$—O, a a single bond, a divalent hydrocarbon radical, and

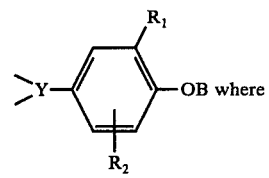

Y is a trivalent hydrocarbon radical, B is a hydrogen atom or the group

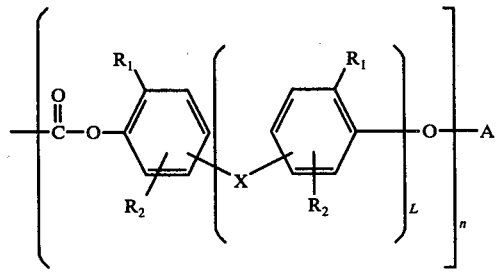

$m$ is 1 to about 20, and $n$ is an average of 0.1 to about 20.

Alkyl groups $R_1$, and $R_2$ have 1 to 10 carbon atoms; cycloalkyl $R_1$ and $R_2$ groups have 5 to 10 carbon atoms and aralkyl groups $R_1$ and $R_2$ have 7 to 10 carbon atoms.

Carbonate esters used in the stabilizer composition of this invention can be prepared by conventional methods by the reaction of a carbonylating agent such as phosgene, a chloroformate ester, a dialkyl carbonate or a diaryl carbonate with the desired orthosubstituted dihydric or trihydric phenol in one or several reaction stages. Acid acceptors such as ammonia, pyridine, organic amines, and inorganic alkalies can be used with phosgene and chloroformate ester, and acidic or alkaline transesterification catalysts can facilitate the reaction of alkyl and aryl carbonate esters. The molecular weight of the carbonate ester is regulated by the proportions of carbonylating agent to ortho-substituted dihydric or trihydric phenol. Thus the product of the reaction between two moles of a dihydric phenol and one mole of carbonylating agent is a relatively low molecular weight mixture of carbonate esters in which the bis(hydroxyaryl carbonate) of the dihydric phenol predominates, and the product of the reaction between 2 moles of a carbonate ester carbonylating agent (e.g. diphenyl carbonate) and one mole of dihydric phenol is a relatively low molecular weight mixture of carbonate esters in which the dihydric phenol bis(phenyl carbonate) ester predominates. The more closely the proportions of carbonylating agent and dihydric or trihydric phenol approach one equivalent of each reactant the higher the molecular weight of the resulting product. In polycarbonates prepared with an excess of the dihydric or trihydric phenol reactant over the carbonylating agent the polycarbonate is predominantly terminated by hydroxyaryl groups while in polycarbonates prepared with an excess of the carbonylating agent over the phenol carbonate ester termination predominates. The hydroxyaryl terminated polycarbonates of average molecular weight ranging from 400 to about 4000 are preferred.

Useful preparative techniques for carbonate esters derived from polyhydric phenols can be found in the disclosures of U.S. Pat. Nos. 3,000,849; 3,028,365 and 3,510,507, as well as the review by L. Bottenbruch in " Encyclopedia of Polymer Science and Technology " (N. Bikales, ed.) Volume 10, pages 714–725 (J.Wiley-Interscience Publishers, New York 1969).

Synthetic resins that can be stabilized with compositions comprising a polyhydric alcohol thioether acid ester and a carbonate ester according to this invention include alphaolefin polymers such as polyethylene, polypropylene, polybutene, poly-3-methylbutene, or copolymers thereof such as ethylene-vinylacetate copolymer, ethylenepropylene polystyrene, polyvinylacetate, acrylic ester resins, copolymers from styrene and another monomer (for example, maleic anhydride, butadiene, acrylonitrile and so on), acrylonitrile-butadiene-styrene copolymer, acrylic acid ester-butadiene-styrene copolymer, methacrylic acid ester-butadiene-styrene copolymer, methacrylate ester resin such as polymethylacrylate, polyvinylalcohol, ethylene and butylene trephthalate polyesters, polyamide, polycarbonate, polyacetal, polyurethane, cellulosic resin, or phenolic resin, urea resin, melamine resin, epoxy resin, unsaturated polyester, silicone resin, halogencontaining resins such as polyvinyl chloride, polyvinylidene chloride, polyvinylidene fluoride and copolymers thereof, and further rubbers such as isoprene rubber chloroprene rubber, and blends of the above resins. Stabilizer compositions comprising a polyhydric alcohol thioether carboxylic acid ester and a carbonate ester according to this invention can be formulated and marketed in liquid, solid, and paste forms. An inert solvent can be used to facilitate handling. The thioether ester and carbonate ester can also be solubilized in one another by heating, such as at 70°–160° C for up to 4 hours, and then allowing the resulting melt to cool and harden sufficiently to be flaked and ground.

Known polymer stabilizers can be used in synthetic resin compositions together with the stabilizer compositions of this invention and can be admixed with the latter. Such known stabilizers include thiodipropionic acid esters, polyvalent metal salts of carboxylic acids, organic phosphites, and 1,2-epoxides.

Representative thiodipropionic acid esters include di-n-dodecyl thiodipropionate, dihexadecyl thiodipropionate, distearyl thiodipropionate, n-octyl eicosanyl thiodipropionate and n-octdecyl cyclohexane-1,4-dimethanol thiodipropionate polyester. A comprehensive disclosure of useful thiodipropionate esters by M. Minagawa et al in U.S. Pat. No. 3,869,423, column 17 line 55 to column 19 line 54 is here incorporated by reference.

Representative polyvalent metal salts include zinc, calcium, magnesium, barium, strontium and nickel salts of monocarboxylic acids having 6 to 24 carbon atoms, for example zinc benzoate, calcium palmitate, and nickel 2-ethylbutyrate. A comprehensive disclosure of useful metal salts by M. Minagawa et al in U.S. Pat. No. 3,869,423, column 19 line 56 to column 20 line 35 is here incorporated by reference.

Representative organic phosphites include triisodecylphosphite, tris (nonylphenyl phosphite), and 4,4'-isopropylidene diphenol $C_{12}$-$C_{15}$ mixed alkyl phosphite. A comprehensive disclosure of useful organic phosphites by M. Minagawa et al in U.S. Pat. No. 3,849,370 Column 13 line 63 to column 16 line 48 is here incorporated by reference.

Representative 1,2-epoxides include epoxysoybean oil, epoxylinseed oil, and 2-ethylhexyl epoxystearate. A comprehensive disclosure of 1,2-epoxides by M. Minagawa et al in U.S. Pat. No. 3,869,423 column 26 line 13 to line 39 is here incorporated by reference.

The preparation of the stabilized resin composition is easily accomplished by conventional procedures. A heated two roll mill, for example, is a convenient compounding tool for blending stabilizer compositions of the invention with polyolefins, vinyl chloride polymers, ABS polymers, ethylene-vinyl acetate copolymers and others.

In the Examples that follow, each stabilizer composition of the invention includes a polyhydric alcohol 3-alkylthiopropionic acid ester from among those listed by name, formula and reference number in Table 1, and a dihydric and trihydric phenol carbonate ester from among those listed by molar porportions of reactants used in their preparation, approximate molecular weight, formula and reference number in Table 2. For the sake of brevity the reference numbers from Table 1 and Table 2 respectively are used in place of the names or formulae of the polyhydric alcohol 3-alkylthiopropionic acid esters (referred to in column headings as polyhydric alcohol thioether ester) and the dihydric and trihydric phenol carbonate esters (referred to in column headings as carbonate ester) to record the results of the stability tests n Tables 3 to 11. Sulfur compounds used in stabilizer compositions not according to this invention for comparison purposes are grouped under heading "Ingredient A" in each of Tables 3 to 11 while the "Ingredient B" column in each such Table groups together carbonate esters and other compounds used in their place instabilizer compositions not of this invention.

Table 1
Polyhydric alcohol thioether carboxylic acid esters Stabilizers

Thioether ester 1:
1,3,5-Tris(n-butylthiopropionyloxyethyl) isocyanurate $$C_4H_9SC_2H_4COC_2H_4-N\overset{\underset{\displaystyle||}{O}}{\phantom{X}}N-C_2H_4OCC_2H_4SC_4H_9$$

with ring substituent $C_2H_4OCC_2H_4SC_4H_9$

Thioether ester 2:
1,3,5-Tris(n-dodecylthiopropionyloxyethyl) isocyanurate $$C_{12}H_{25}SC_2H_4COC_2H_4-N\phantom{XX}N-C_2H_4OCC_2H_4SC_{12}H_{25}$$

with ring substituent $C_2H_4OCC_2H_4SC_{12}H_{25}$

Thioether ester 3:
1,3-Bis(n-octadecylthiopropionyloxyethyl)-5-hydroxyethyl isocyanurate $$C_{18}H_{37}SC_2H_4COC_2H_4-N\phantom{XX}N-C_2H_4OCC_2H_4SC_{18}H_{37}$$

with ring substituent $C_2H_4OH$

Thioether ester 4:
Thiorimethylolethanetris(n-octhylthiopropionate)

$$\left(C_8H_{17}SC_2H_4COCH_2\right)_3 C-CH_3$$

Thioether ester 5:
Trimethylolethanetris(3-n-dodecylthiopropionate)

$$\left(C_{12}H_{25}SC_2H_4COCH_2\right)_3 C-CH_3$$

Thioether ester 6:
Trimethylolethanebis(3-n-dodecylthiopropionate)

$$\left(C_{12}H_{25}SC_2H_4COCH_2\right)_2 C-CH_2OH \atop CH_3$$

Thioether ester 7:
Trimethylolpropanetris(3-n-dodecylthiopropionate)

$$\left(C_{12}H_{25}SC_2H_4COCH_2\right)_3 C-C_2H_5$$

Table 1-continued
Polyhydric alcohol thioether carboxylic acid esters Stabilizers Thioether ester 8:
Trimethylolpropanetris(n-octadecylthiopropionate)

$$\left(C_{18}H_{37}SC_2H_4COCH_2\right)_3 C-C_2H_5$$

Thioether ester 9:
Trimethylolpropanebis(3-n-octadecylthiopropionate)

$$\left(C_{18}H_{37}SC_2H_4COCH_2\right)_2 C-CH_2OH \atop C_2H_5$$

Thioether ester 10:
Pentaerythritol tetrakis(3-n-butylthiopropionate)

$$\left(C_4H_9SC_2H_4COCH_2\right)_4 C$$

Thioether ester 11:
Pentaerythritol tetrakis(3-n-dodecylthiopropionate)

$$\left(C_{12}H_{25}SC_2H_4COCH_2\right)_4 C$$

Thioether ester 12:
Pentaerythritol tetrakis(3-n-octadecylthiopropionate)

$$\left(C_{18}H_{37}SC_2H_4COCH_2\right)_4 C$$

Thioether ester 13:
1,3,5-Tris(3-n-octyl thio-2-methylpropionyloxyethyl)isocyanurate $$C_8H_{17}SCH_2CHCOC_2H_4-N\phantom{XX}N-C_2H_4OCCHCH_2SC_8H_{17}$$

with $CH_3$ branches and ring substituent $C_2H_4OCCHCH_2SC_8H_{17}$ / $CH_3$

Thioether ester 14:
Trimethylolethanetris(3-n-octadecylthio-2-methylpropionate)

$$\left(C_{18}H_{37}SCH_2CHCOCH_2\right)_3 C-CH_3 \atop CH_3$$

Thioether ester 15:
Trimethylolpropanetris(3-n-octylthio-2-methylpropionate)

$$\left(C_8H_{17}SCH_2CHCOCH_2\right)_3 C-C_2H_5 \atop CH_3$$

Thioether ester 16:
Pentaerythritol tris(3-(2-ethylhexylthio)-2-methylpropionate)

$$\left(C_4H_9CHCH_2SCH_2HCOCH_2\right)_3 C-CH_2OH \atop C_2H_5 \phantom{XXX} CH_3$$

TABLE 2
Carbonate Ester Stabilizers

Carbonate ester 1:
2,5-Di-t-butylhydroquinone/diphenyl carbonate, 8:7 molar ratio

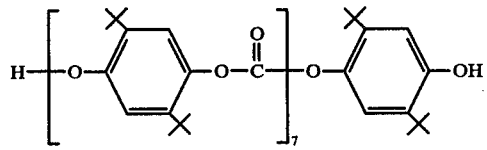

Approximate molecular weight 2100

Carbonate ester 2:
2,5-Di-T-butylhydroquinone/diphenyl carbonate, 9:10 molar ratio

TABLE 2-continued
Carbonate Ester Stabilizers

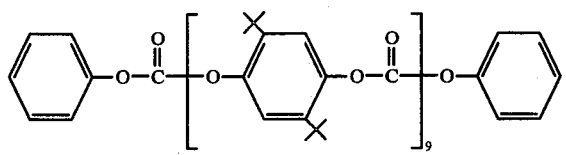

Approximate molecular weight 2400

Carbonate ester 3:
4,4'-Methylenebis(2-t-butyl-6-methylphenol)/diphenyl carbonate, 3:2 molar ratio

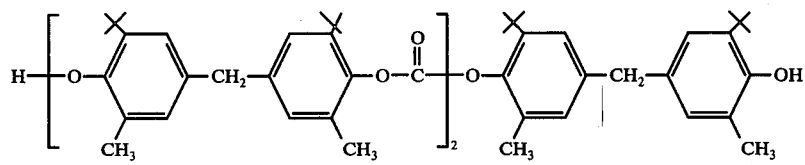

Approximate molecular weight 1100

Carbonate ester 4:
4,4'-Butylidenebis(2-t-butyl-5-methylphenol)/diphenyl carbonate, 2:1 molar ratio

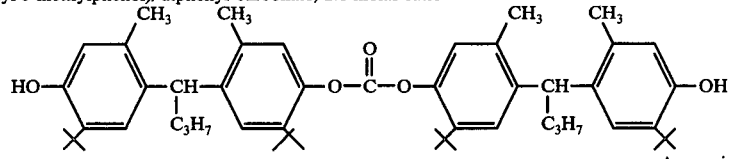

Approximate molecular weight 700

Carbonate ester 5:
4,4'-Butylidenebis(2-t-butyl-5-methylphenol)/diphenyl carbonate, 4:3 molar ratio

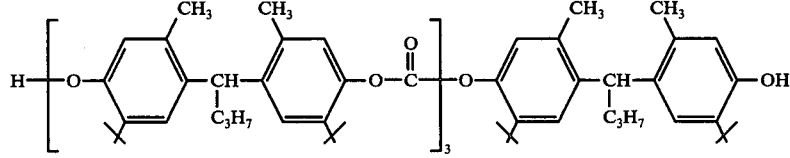

Approximate molecular weight 1500

Carbonate ester 6:
4,4'-Butylidenebis(2-t-butyl-5-methylphenol)/diphenyl carbonate, 6:5 molar ratio

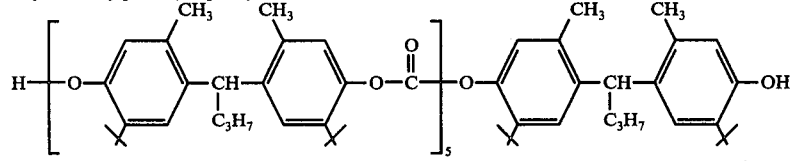

Approximate molecular weight 2300

Carbonate ester 7:
4,4'-Thiobis(2-t-butyl-5-methylphenol)/diphenyl carbonate, 4:3 molar ratio

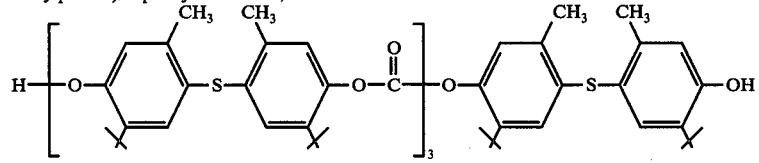

Approximate molecular weight 1500

Carbonate ester 8
4,4'-Thiobis(2-t-butyl-5-methylphenol)/diphenyl carbonate, 2:3 molar ratio

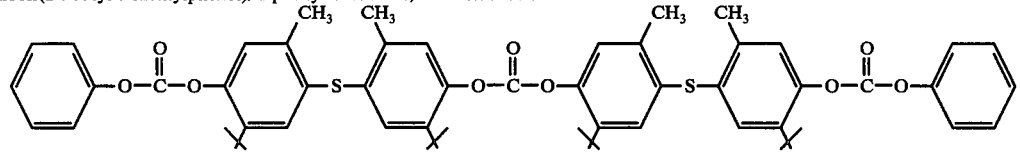

Approximate molecular weight 1000

Carbonate ester 9:
Bis(2-methyl-4-hydroxy-5-t-butylbenzyl) sulfide/dipneyl carbonate, 8:7 molar ratio

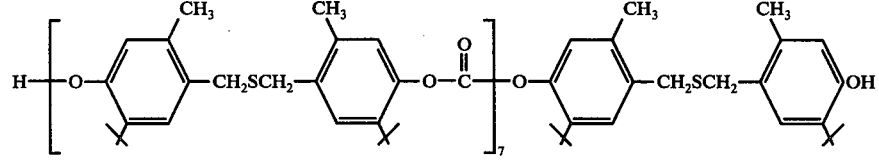

Approximate molecular weight 2400

TABLE 2-continued
Carbonate Ester Stabilizers

Carbonate ester 10:

Bis(2-methyl-4-hydroxy-5-t-butylbenzyl) sulfide/diphenyl carbonate, 4:3 molar ratio

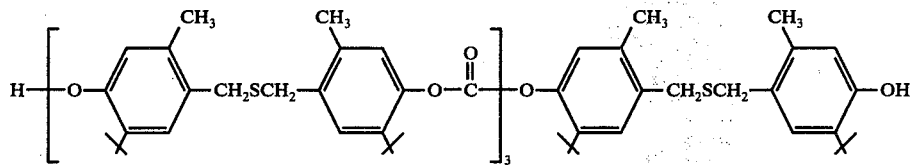

Approximate molecular weight 1600

Carbonate ester 11:

4,4'Cyclohexylidenebis(2-cyclohexylphenol)/diphenyl carbonate, 5:4 molar ratio

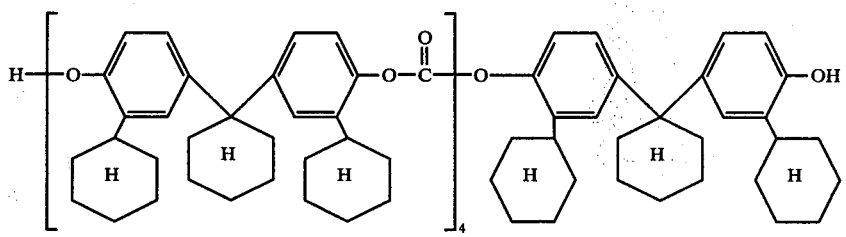

Approximate molecular weight 2300

Carbonate ester 12:

4,4'-Cyclohexylidenebis(2-cyclohexylphenol)/diethyl carbonate, 5:6 molar ratio

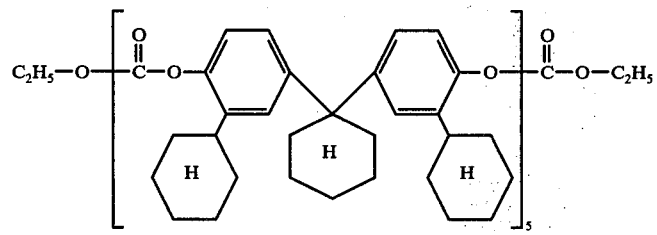

Approximate molecular weight 2400

Carbonate ester 13:

2,2'Methylenebis(4-methyl-6-t-butylphenol)/dipenyl carbonate, 3:2 molar ratio

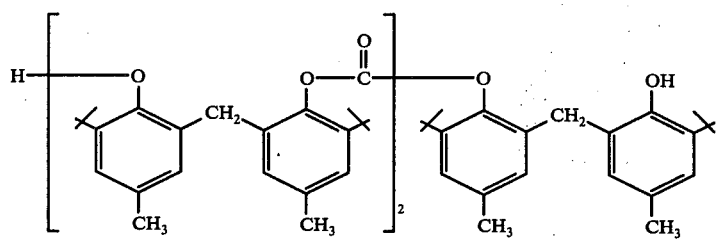

Approximate molecular weight 1100

Carbonate ester 14:

2,2'-Methylenebis(4-methyl-6-t-butylphenol)/diphenyl carbonate, 6:5 molar ratio

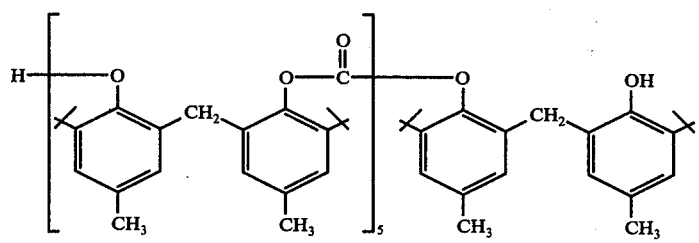

Approximate molecular weight 2200

Carbonate ester 15:

1-(3',5'-Di-t-butyl-4'-hydroxyphenyl)-3,3-di-(3'-t-butyl-4'-hydroxyphenyl)butane/diphenyl carbonate, 2:1 molar ratio

TABLE 2-continued

Carbonate Ester Stabilizers

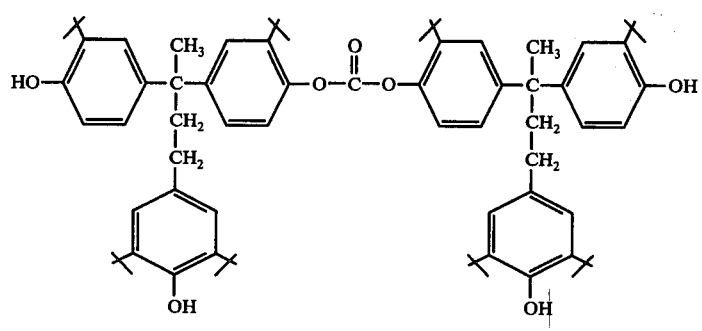

Approximate molecular weight 1100

Carbonate ester 16:

1(3',5'-Di-t-butyl-4'-hydroxyphenyl)-3,3-di-(3'-t-butyl-4'hydroxyphenyl)butane/diphenyl carbonate, 4:3 molar ratio

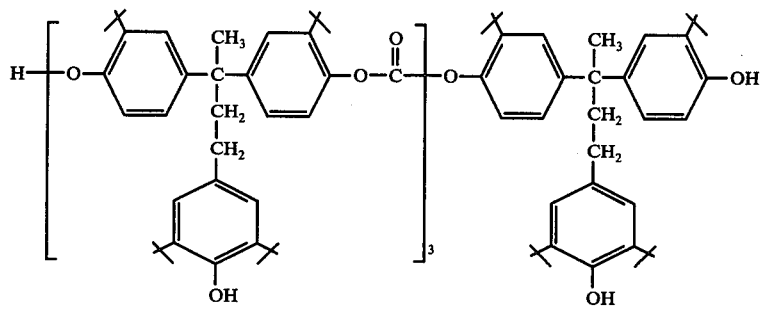

Approximate molecular weight 2200

Carbonate ester 17:

1-(3',5'-Di-t-butyl-4'-hydroxyphenyl)-3,3-di-(3'-t-butyl-4'-hydroxyphenyl)butane/diphenyl carbonate, 8:7 molar ratio

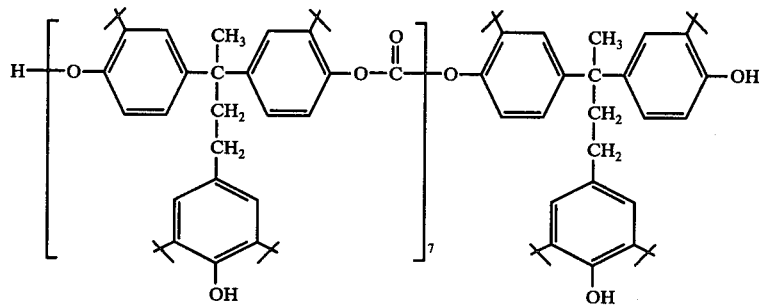

Approximate molecular weight 3700

Carbonate ester 18:

1,1,3-Tris(2'-methyl4'-hydroxy-5'-t-butyl-phenyl)butane/diphenyl carbonate, 2:1 molar ratio

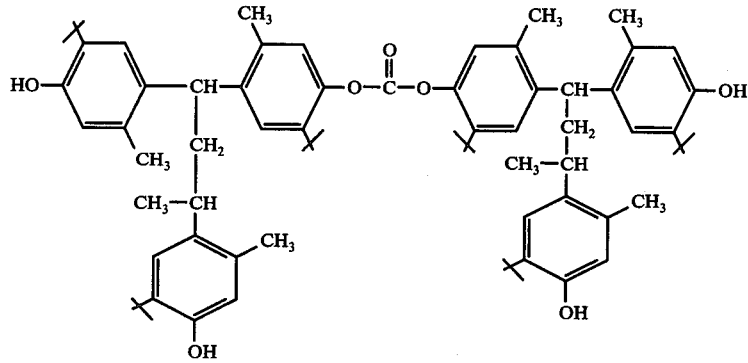

Approximate molecular weight 1100

Carbonate ester 19:

1,1,3-Tris(2'-methyl-4'-hydroxy-5'-t-butyl-phenyl)butane/diphenyl carbonate, 5:4 molar ratio

TABLE 2-continued

Carbonate Ester Stabilizers

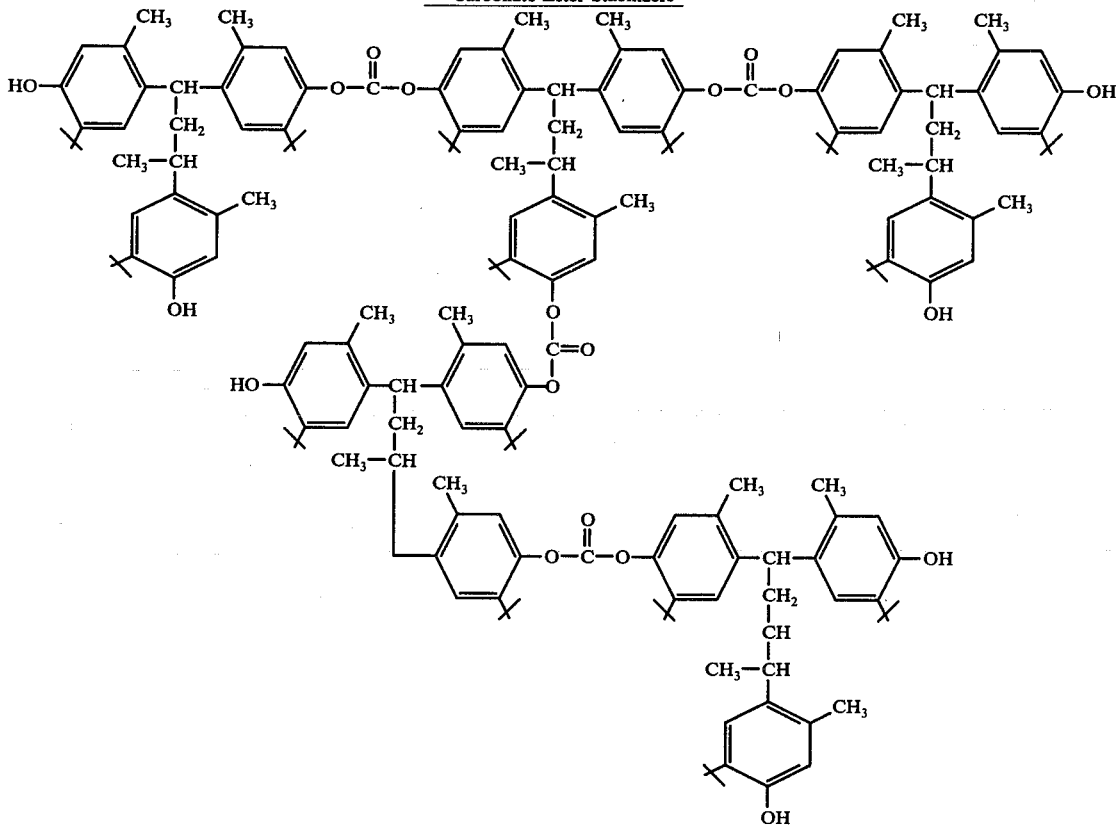

Approximate molecular weight 2700

Carbonate ester 20:
4,4'Thiobis(2-t-butyl-6-methylphenol/diphenyl carbonate, 2:1 molar ratio

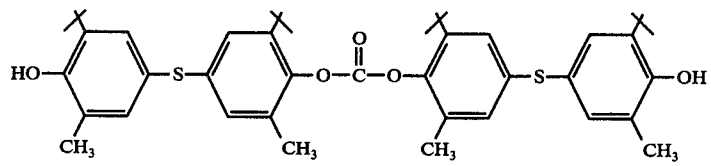

Approximate molecular weight 700

Carbonate ester 21:
4,4'-Butylidenebis(2-t-butyl-5-methylphenol/4,4'-thiobis(2-t-butyl-5-methyl)phenol bischloroformate, 3:2 molar ratio

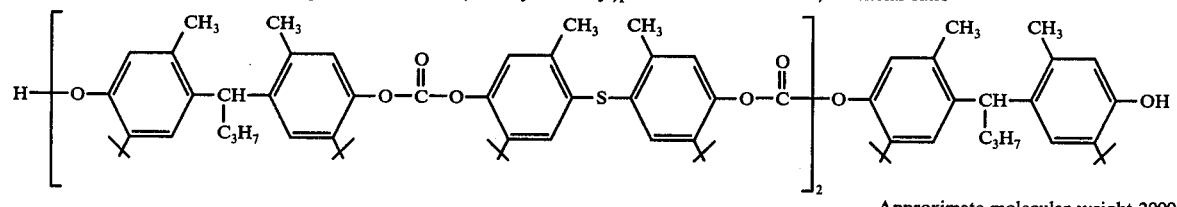

Approximate molecular weight 2000

EXAMPLES 1 TO 10

In order to examine the stabilizing effect of stabilizer compositions according to this invention, un-stabilized polypropylene resin 100 parts by weight, thioether carboxylic acid ester of the invention or dilauryl thiodipropionate 0.15 part by weight and a caarbonate ester or BHT antioxidant 0.1 part by weight were ground together for 10 minutes at room temperature. This mixed powder blend was kneaded on a two roll mill at 180° C for six minutes and from the mill stock a sheet of 1.0 mm in thickness was prepared by compression molding at 180° C and 200 kg/cm² for 5 minutes. Each molded sheet was cut to the size of 40 × 150 mm, and suspended in an individual glass cyclinder.

Each cylinder was set in an air circulating oven at 160.5° C, flushed with pure oxygen, the pressure adjusted to one atmosphere, and the cylinder fitted with a closed manometer. The time to beginning of oxidation-degradation was read by recording the time when the pressure in the cylinder diminished rapidly. The ingredients of the stabilizer combination used in each example and the results observed as shown in Table 3.

TABLE 3

| Ingredient | Ingredient | Time to Begin Degradation |
| --- | --- | --- |

TABLE 3-continued

| Control | A | B | (hours) |
|---|---|---|---|
| A | Dilauryl thiodipropionate | BHT Antioxidant | 20 |
| B | Dilauryl thiodipropionate | Carbonate ester No. 3 (Table 2) | 76 |
| C | (None) | Carbonate ester No. 15 | 28 |
| D | Thioether ester No. 2 (Table 1) | BHT Antioxidant | 64 |
| E | Thioether ester No. 11 | (None) | 18 |

| Example | Polyhydric Alcohol Thioether Ester (Table 1) | Carbonate Ester (Table 2) | Time to Begin Degradation (hours) |
|---|---|---|---|
| 1 | No. 1 | No. 12 | 132 |
| 2 | No. 2 | No. 3 | 138 |
| 3 | No. 5 | No. 7 | 121 |
| 4 | No. 6 | No. 17 | 114 |
| 5 | No. 8 | No. 15 | 127 |
| 6 | No. 9 | No. 4 | 120 |
| 7 | No. 10 | No. 10 | 140 |
| 8 | No. 11 | No. 14 | 145 |
| 9 | No. 13 | No. 21 | 117 |
| 10 | No. 15 | No. 5 | 123 |

The results of these experiments demonstrate the synergistic interaction of the polyhydric alcohol thioether carboxylic acid ester and the carbonate ester in the combination according to this invention. The observed times to the beginning of degradation as shown by a drop in oxygen pressure are far greater for the combinations of Examples 1 to 10 than for a thioether ester along (Control E), a carbonate ester alone (Control C), or a combination of a carbonate ester with dilauryl thiodipropionate, a thioether carboxylic acid ester not of the type selected for the combination of this invention (Control B).

EXAMPLES 11 to 20

Substantially unstabilized polypropylene resin (Profax 6501, containing a trace of BHT antioxidant to protect the polymer during shipment and storage only) 100 parts by weight, dilauryl-thiodipropionate 0.2 part by weight, polyhydric alcohol thioether carboxylic acid ester or additional dilaurylthiodipropionate 0.1 part and a carbonate ester (Table 2) 0.1 part by weight were mixed for ten minutes by mixing and grinding at room temperature and milled and molded to make a sheet of 1.0 mm in thickness under the condition mentioned in Examples 1–10. This sheet was cut into ten sample pieces of 10 × 20 mm of each formulation, and exposed on aluminum foil in a Geer air-circulating oven at 160° C for heat stability examination. The time to the beginning of degradation was taken as the time when more than five sample pieces in ten of each formulation were discolored and brittle. The stabilizer ingredients used and the results obtained are shown in Table 4.

TABLE 4

| Control | Ingredient A | Ingredient B | Time to Begin Degradation (hours) |
|---|---|---|---|
| F | Dilaurylthiodipropionate | Carbonate ester No. 5 (Table 2) | 720 |
| G | Ethyleneglycol bis (laurylthiopropionate) | Carbonate ester No. 19 | 760 |
| H | Thioether ester No. 7 (Table 1) | 4,4'-n-butylidene-bis(2-t-butyl-5-methylphenol) | 480 |
| I | Thioether ester No. 13 | Carbonate ester of 4,4'-isopropylidenediphenol, mol. wt. approx. 1000 | 290 |

| Example | Alcohol Thioether Ester (Table 1) | Carbonate Ester (Table 2) | Time to Begin Degradation (hours) |
|---|---|---|---|
| 11 | No. 2 | No. 16 | 1,070 |
| 12 | No. 3 | No. 9 | 1,190 |
| 13 | No. 4 | No. 20 | 1,210 |
| 14 | No. 5 | No. 5 | 1,160 |
| 15 | No. 7 | No. 10 | 1,050 |
| 16 | No. 11 | No. 19 | 1,230 |
| 17 | No. 12 | No. 17 | 980 |
| 18 | No. 13 | No. 8 | 1,120 |
| 19 | No. 14 | No. 13 | 1,270 |
| 20 | No. 16 | No. 2 | 1,140 |

The observed times to the beginning of degradation as shown by becoming discolored and brittle are far greater for the compositions according to this invention than for the control samples that are lacking one or the other essential ingredient, thus demonstrating the enhanced effectiveness of the stabilizer compositions according to this invention. The excellent results of Example 18 contrast with Control 1, which contains a carbonate ester lacking the essential $R_1$ alkyl substituent required according to this invention, and has less than one third the heat stability of Example 18. Similarly, Example 15 compares favorably with Control H, which has the same polyhydric alcohol thioether ester but a conventional phenolic antioxidant instead of a carbonate ester according to this invention, and has less than half the heat stability of Example 15. Since all samples contain as part of the base formulation 0.2 part by weight of dilauryl thiodipropionate, the contrast between Example 14 and Control F is particularly significant. Both Example 14 and Control F contain the same about 1500 molecular weight carbonate ester of 4,4'-butylidenebis(2-t-butyl-5-methyl)phenol; Example 14 contains 0.1 part of trimethylolethanetris (3-dodecylthiopropionate) while Control F contains 0.1 part additional dilauryl thiodipropionate. Yet, Example 14 has more than 60% greater heat stability, which demonstrates that the polyhydric alcohol ester used according to this invention acts in a different manner from the conventional dilauryl thiodipropionate. The same considerations also apply to a comparison of Example 16 with Control G.

EXAMPLES 21-30

Stabilized polyethylene resin (Hi-Zex 5100E, Mitsui Petrochemical Industries, Ltd. Japan) 100 parts by weight, a polyhydric alcohol thioether carboxylic acid ester 0.1 part and a carbonate ester compound 0.05 part by weight were milled on a two roll mill for 5 minutes at 150° C and then molded into a sheet of 1.2 mm thickness by compression molding at 150° C and 180 kg/cm² for 5 minutes. The sheet was cut into sample pieces of 10 × 20 mm and tested for heat stability in the Geer oven at 148.5° C in air on aluminum foil. The time to the beginning of degradation was taken as the time when more than five sample pieces in ten of each formulation were discolored and brittle. The stabilizer ingredients used and the results obtained are shown in Table 5.

TABLE 5

| Control | Ingredient A | Ingredient B | Time to Begin Degradation (hours) |
|---|---|---|---|
| J | (None) | (None) | 173 |
| K | Distearyl thiodipropionate | Carbonate ester No. 6 (Table 2) | 317 |
| L | Thioether ester No. 5 (Table 1) | Carbonate ester of 4,4'-isopropyli- | |

TABLE 5-continued

| Example | Polyhydric Alcohol Thioether Ester (Table 1) | Carbonate Ester (Table 2) | Time to Begin Degradation (hours) |
|---|---|---|---|
| | dene diphenol (Table 4) | | 236 |
| 21 | No. 1 | No. 4 | 481 |
| 22 | No. 2 | No. 6 | 464 |
| 23 | No. 5 | No. 3 | 505 |
| 24 | No. 6 | No. 18 | 463 |
| 25 | No. 7 | No. 11 | 490 |
| 26 | No. 8 | No. 14 | 452 |
| 27 | No. 10 | No. 15 | 476 |
| 28 | No. 11 | No. 12 | 487 |
| 29 | No. 12 | No. 20 | 475 |
| 30 | No. 13 | No. 1 | 517 |

The results of these tests demonstrate the surprisingly powerful protection obtained with combinations of polyhydric alcohol thioether carboxylic acid ester and carbonate ester according to this invention, as compared to the relative ineffectiveness of superficially similar combinations lacking an essential feature of this invention. The excellent results of Example 23 contrast with Control L which contains a carbonate ester lacking the essential $R_1$ alkyl substituent required according to this invention and provides less than one half the heat stability. Also, Example 22 with 1,3,5-tris (3-dodecylthiopropionyloxyethyl)isocyanurate and the approx. 2300 molecular weight carbonate of 4,4'-butylidenebis(2-t-butylphenol) is very much better in heat stability than Control K with the same carbonate ester and distearyl thiodipropionate.

EXAMPLES 31 to 40

ABS resin (Blendex 111) 100 parts by weight, zinc stearate 0.5 part by weight, titanium oxide 5.0 parts by weight, thioether ester 0.2 part and a carbonate ester 0.2 part by weight were mixed by grinding at room temperature for 10 minutes.

The compound was prepared by extruding the ground mixture using a 30 mm extruder at 30 rpm and 240° C. A sheet of 0.5 mm thickness was prepared by compression molding and compound at 200 kg/cm² and 180° C for 5 minutes. The heat stability test was carried out in the same way as examples 1–10 except that the test temperature was at 140° C.

The stabilizer ingredients used and the results obtained are shown in Table 6.

Table 6

| Control | Ingredient A | Ingredient B | Time to Begin Degradation (Min.) |
|---|---|---|---|
| M | (None) | Carbonate Ester No. 1 (Table 2) | 210 |
| N | Distearyl Thiodipropionate | Carbonate Ester No. 10 | 200 |
| O | Thioether ester No. 1 (Table 1) | (None) | 200 |
| P | Thioether ester No. 9 | BHT Antioxidant | 290 |

| Example | Polyhydric Alcohol Thioether ester (Table 1) | Carbonate Ester (Table 2) | Time to Begin Degradation (Min.) |
|---|---|---|---|
| 31 | No. 1 | No. 21 | 620 |
| 32 | No. 3 | No. 10 | 660 |
| 33 | No. 4 | No. 7 | 670 |
| 34 | No. 6 | No. 20 | 550 |
| 35 | No. 7 | No. 1 | 690 |
| 36 | No. 9 | No. 18 | 570 |
| 37 | No. 11 | No. 16 | 530 |
| 38 | No. 14 | No. 11 | 610 |
| 39 | No. 15 | No. 3 | 590 |
| 40 | No. 16 | No. 13 | 580 |

The results of this experiment show the great synergistic effectiveness of the stabilizer compositions of this invention in ABS polymer. Thus Example 36 of this invention can be compared with Control P which contains the same polyhydric alcohol thioether carboxylic acid ester with a conventional phenolic antioxidant instead of a carbonate ester of this invention. The sample of Control P had only about one half the heat stability as measured by the time to a sudden decrease in oxygen pressure as the sample of Example 36 according to this invention. Comparison of Example 32 with Control N shows that the same approximately 1600 molecular weight carbonate of bis(2-methyl-4-hydroxy-5-t-butylbenzyl) sulfide provides twice the heat stability in the Example 32 composition of this invention together with 1,3,5-tris(3-octadecylthiopropionyloxyethyl) isocyanurate as in the Control N composition with distearyl thiodipropionate.

EXAMPLES 41 TO 50

A clear sheet was prepared by kneading polyvinylchloride resin (Geon 103EP) 100 parts, dioctylphthalate 42 parts, epoxidized soybean oil 3 parts, zinc stearate 0.3 part, barium stearate 0.5 part, stearic acid 0.3 part, a thioether ester 0.2 parts, and a carbonate ester 0.05 part on a two roll mill at 175° C for 5 minutes and then compression molding at 175° C. Then, a heat stability test was carried out in a Geer oven at 190° C in an air atmosphere. The time to degradation was determined by the discoloration observed. The organic phosphite and carbonate used and the results obtained are shown in Table 7.

Table 7

| Control | Ingredient A | Ingredient B | Time to Yellow | Time to Black |
|---|---|---|---|---|
| | | | Degradation Mins. | |
| Q | None | Carbonate ester No. 17 (Table 2) | 35 | 45 |
| R | Dilauryl Thiodipropionate | Carbonate ester No. 8 | 40 | 50 |
| S | Thioether ester No. 4 (Table 1) | None | 40 | 45 |
| T | Thioether ester No. 10 | Stearylbeta 3,5-di-t-butyl-4-hydroxyphenyl propionate | 45 | 55 |

| Example | Polyhydric Alcohol Thioether Ester (Table 1) | Carbonate Ester (Table 2) | Time to Yellow | Time to Black |
|---|---|---|---|---|
| | | | Degradation Mins. | Mins. |
| 41 | No. 2 | No. 17 | 65 | 85 |
| 42 | No. 4 | No. 21 | 60 | 80 |
| 43 | No. 5 | No. 14 | 60 | 75 |
| 44 | No. 7 | No. 19 | 65 | 80 |
| 45 | No. 8 | No. 9 | 70 | 85 |
| 46 | No. 10 | No. 5 | 65 | 85 |
| 47 | No. 11 | No. 15 | 60 | 80 |
| 48 | No. 12 | No. 12 | 65 | 90 |
| 49 | No. 14 | No. 8 | 70 | 90 |
| 50 | No. 15 | No. 2 | 70 | 85 |

The results show the unexpectedly large contribution to PVC heat stability provided by the compositions according to this invention. Thus, pentaerythritol tetrakis(3-butylthiopropionate) with the carbonate ester of 4,4'-butylidene bis(2-t-butyl-5-methylphenol) (Example 46) provides far greater stabilization than the thioether ester used with a known phenolic antioxidant (Control T) usually considered highly effective, and Example 49 contrasted with Control R provides a measure of the superiority of trimethylolethane tris (3-octadeclthio-2-methylpropionate) in a composition of this invention with 4,4'-thiobis(2-t-butyl-5-methylphenol) carbonate ester over dilauryl thiodipropionate used with the same carbonate ester.

EXAMPLES 51 to 60

100 parts of nylon 66 delustered by adding 0.05% of titanium dioxide was dissolved in 90 parts of 90% formic acid, and a polyhydric alcohol thioether carboxylic acid ester 0.5 part and a carbonate ester 0.3 part were added and mixed completely. The solution was flowed uniformly on a glass plate, and dried in a heated air oven at 105° C for 10 minutes to prepare a film. The color of the film, after being heated in an air oven at 225° C for 30 minutes, was measured and shown in Table 8 along with the compounds present in each formulation.

Table 8

| Control | Ingredient A | Ingredient B | Color |
|---|---|---|---|
| U | None | None | Dark Brown |
| V | Distearyl thio-dipropionate | Carbonate Ester No. 20 (Table 2) | Yellow |
| W | Thioether ester No. 14 (Table 1) | BHT Antioxidant | Yellow |
| X | Distearyl thio-dipropionate | BHT Antioxidant | Light Brown |
| Example | Polyhydric Alcohol Thioether Ester (Table 1) | Carbonate Ester (Table 2) | Color |
| 51 | No. 1 | No. 8 | Pale Yellow |
| 52 | No. 3 | No. 1 | Pale Yellow |
| 53 | No. 4 | No. 6 | Pale Yellow |
| 54 | No. 8 | No. 20 | Pale Yellow |
| 55 | No. 9 | No. 13 | Very Pale Yellow |
| 56 | No. 11 | No. 17 | Very Pale Yellow |
| 57 | No. 12 | No. 4 | Pale Yellow |
| 58 | No. 13 | No. 15 | Pale Yellow |
| 59 | No. 14 | No. 3 | Very Pale Yellow |
| 60 | No. 16 | No. 21 | Very Pale Yellow |

These experiments prove the unexpected superiority in protecting the color of the polyamide of combinations according to this invention such as Examples 54 and 59 over individual components or combinations lacking one or both of the essential components such as Controls W and U containing respectively trimethylolethane tris (3-octadecylthio-2-methylpropionate) with BHT antioxidant instead of a carbonate ester and distearyl thiodipropionate instead of a polyhydric alcohol thioether with 4,4'-thiobis(2-t-butyl-5-methylphenol carbonate of approximate molecular weight 700.

EXAMPLES 61 to 70

In order to examine the effect of the stabilizer owing to this invention on polybutene resin, a sheet of 1 mm in thickness was prepared by kneading the following formulation on a two roll mill and then compression molding at 160° C and 200 kg/cm² for 5 minutes.

The sheet obtained was cut to the size of 40 × 150 mm, and tested for heat stability at 160° C in glass cylinders containing pure oxygen at 1 atmosphere pressure as in Examples 1-10.

| (Formulation) | parts by weight |
|---|---|
| Un-stabilized poly-1-butene resin | 100 |
| Calcium stearate | 1.0 |
| Distearylthiodipropionate | 0.1 |
| Polyhydric alcohol thioether carboxylic acid ester | 0.1 |
| Carbonate ester | 0.1 |

The results are shown in Table 9. The time to beginning of oxidation degradation was read by recording the time when the pressure in the cylinder diminished rapidly.

Table 9

| Control | Ingredient A | Ingredient B | Time to Begin Degradation (hours) |
|---|---|---|---|
| Y | None | Carbonate ester of 4,4'-isopropylidene-diphenol (Table 4) | 40 |
| Z | Thioether ester No. 15 (Table 1) | Carbonate ester of 4,4'-isopropylidenediphenol (as above) | 110 |
| AA | None | Carbonate ester No. 21 (Table 2) | 85 |
| BB | Dilauryl thio-dipropionate | Carbonate ester No. 4 | 160 |
| Example | Polyhydric Alcohol Thioether Ester (Table 1) | Carbonate Ester (Table 2) | Time To Begin Degradation (hours) |
| 61 | No. 1 | No. 16 | 410 |
| 62 | No. 2 | No. 7 | 435 |
| 63 | No. 4 | No. 18 | 420 |
| 64 | No. 5 | No. 15 | 390 |
| 65 | No. 7 | No. 21 | 460 |
| 66 | No. 8 | No. 4 | 385 |
| 67 | No. 10 | No. 8 | 350 |
| 68 | No. 11 | No. 3 | 455 |
| 69 | No. 15 | No. 20 | 445 |
| 70 | No. 16 | No. 5 | 460 |

These examples demonstrate the unexpectedly great stabilizing effectiveness of combinations of this invention in polybutene. The contrast between Example 69 and Control Z, where trimethylolpropane tris(3-octylthio-2-methylpropionate) (the same as in Example 69) is used together with a carbonate ester lacking the essential $R_1$ alkyl group according to this invention is especially noteworthy, Example 69 providing four times the heat stability of Control Z.

EXAMPLES 71 to 80

In order to examine the effects of the combinations according to this invention in ethylene-vinylacetate copolymer, samples were prepared according to the following formulation and tested for heat stability in a Geer oven at 175° C and initial color was measured for yellowness using the Hunter color difference meter, greater numbers indicating more severe discoloration.

The results are shown in Table 10. The heat stability is expressed in minutes of heating in the oven until a red or brown discoloration was observed.

| (Formulation) | parts |
|---|---|
| Ethylene-Vinylacetate copolymer resin | 100 |
| Montan wax ester lubricant | 0.3 |
| Polyhydric alcohol thioether carboxylic acid ester | 0.1 |

-continued

| (Formulation) | parts |
|---|---|
| Carbonate ester | 0.05 |

Table 10

| Control | Ingredient A | Ingredient B | Time to begin Degradation (Min.) | Color |
|---|---|---|---|---|
| CC | None | None | 75 | 34 |
| DD | None | Carbonate ester No. 4 (Table 2) | 90 | 18 |
| EE | Dilauryl Thiodipropionate | Carbonate ester No. 7 | 105 | 14 |
| FF | Thioether ester No. 14 (Table 1) | NONE | 90 | 19 |
| GG | Thioether ester No. 8 | BHT antioxidant | 105 | 16 |

| Ex. | Polyhydric Alcohol Thioether Ester (Table 1) | Carbonate Ester (Table 2) | Time to Begin Degradation (min.) | Initial Color |
|---|---|---|---|---|
| 71 | No. 2 | No. 20 | 165 | 9 |
| 72 | No. 3 | No. 3 | 150 | 8 |
| 73 | No. 5 | No. 4 | 150 | 10 |
| 74 | No. 7 | No. 16 | 135 | 7 |
| 75 | No. 8 | No. 18 | 150 | 9 |
| 76 | No. 11 | No. 5 | 165 | 10 |
| 77 | No. 12 | No. 19 | 135 | 8 |
| 78 | No. 13 | No. 7 | 165 | 11 |
| 79 | No. 14 | No. 15 | 150 | 9 |
| 80 | No. 15 | No. 1 | 150 | 10 |

These experiments demonstrate the surprising advantages of stabilizer compositions according to this invention over compositions lacking one or both of the essential ingredients according to the invention. Thus Example 75 containing trimethylolpropane tris(3-n-octadecylthiopropionate) and the approximately 1100 mol. wt. carbonate ester of 1,1,3-tris(2'-methyl-4'-hydroxy-5'-t-butylphenyl) butane according to this invention compares very favorably to Control GG in which the same thioether ester is used together with a conventional antioxidant, and Example 78 containing 1,3,5-tris (3-n-octylthio-2-methylpropionyloxyethyl) isocyanurate and the approximately 1500 mol. wt. carbonate ester of 4,4'-thiobis(2-t-butyl-5-methylphenol) compared to Control EE containing the same carbonate ester with dilauryl thiodipropionate not of this invention is far superior in both initial color and heat stability.

EXAMPLES 81 to 90

The stabilizer combinations according to this invention have an excellent stabilizing effect on crosslinked polyethylene. Unstabilized low density polyethylene (meltindex 2.0) 100 parts by weight, dilaurylthiodipropionate 0.1 part by weight, polyhydric alcohol thioether carboxylic acid ester or additional dilaurylthiodipropionate 0.1 part, and a carbonate ester 0.1 part by weight were mixed by milling on a two roll mill at 110° C for 10 minutes and then dicumyl peroxide (Percumyl D, Nippon Oil and Fats Co. Ltd.), 2.0 parts by weight was added and further kneaded at the same temperature for two minutes. This sheet prepared on the mill was compression molded at 110° C and 100 kg/cm² for 5 minutes, then rapidly heated up to 180° C while maintaining the pressure at 100 kg/cm² for 15 minutes. The sheet obtained was cut to the size of 40 × 150 mm, hung in a Geer oven and tested for heat stability in air at 160° C. The degradation time was judged by looking for the time when more than 50% of pieces were discolored or deformed. The stabilizers ingredients used and the results obtained are shown in Table 11.

Table 11

| Control | Ingredient A | Ingredient B | Time to Begin Degradation (hours) |
|---|---|---|---|
| HH | None | Carbonate ester No. 16 (Table 2) | 52 |
| II | Dilaurylthiodipropionate | Carbonate ester No. 18 | 86 |
| JJ | Thioether ester No. 12 | 4,4'-thiobis(2-t-butyl-5-methylphenol) | 95 |
| KK | Dilaurylthiodipropionate | 4,4'-thiobis(2-t-butyl-5-methylphenol) | 79 |

| Example | Polyhydric Alcohol Thioether Ester (Table 1) | Carbonate Ester (Table 2) | Time to Begin Degradation (hours) |
|---|---|---|---|
| 81 | No. 1 | No. 6 | 169 |
| 82 | No. 3 | No. 8 | 176 |
| 83 | No. 4 | No. 9 | 162 |
| 84 | No. 6 | No. 16 | 164 |
| 85 | No. 9 | No. 21 | 175 |
| 86 | No. 10 | No. 2 | 180 |
| 87 | No. 11 | No. 11 | 187 |
| 88 | No. 12 | No. 18 | 159 |
| 89 | No. 13 | No. 13 | 168 |
| 90 | No. 15 | No. 4 | 153 |

The results of these tests demonstrate the great stabilizing effectiveness in cross-linked polyethylene of the compositions according to the invention, which compare favorably to single stabilizers and to combinations of stabilizers not of this invention. Thus pentaerythritol tetrakis(3-n-octadecylthiopropionate) is used in Control JJ in combination with a phenolic antioxidant and in Example 88 in combination with the approx. 1100 molecular weight carbonate ester of 1,1,3-tris(2'-methyl-4'-hydroxy-5'-t-butylphenyl) butane according to this invention, and the latter combinations had 67% greater heat stability than the control composition. Similarly, Example 88 had more than 85% greater heat stability than Control 11 in which the same carbonate ester was combined with dilauryl thiodipropionate.

We claim:

1. A stabilizer composition useful in synergistically increasing the resistance of a synthetic resin to deterioration when heated comprising in combination (a) at least one thioether ester of a polyhydric alcohol having 5 to 15 carbon atoms and 3 to 8 primary hydroxyl groups with a 3-alkylthiopropionic acid having 4 to about 34 carbon atoms, and (b) at least one 400 to 4000 molecular weight carbonate ester terminating in a phenolic hydroxyl, alkyl carbonate, or phenyl carbonate group, and having the formula:

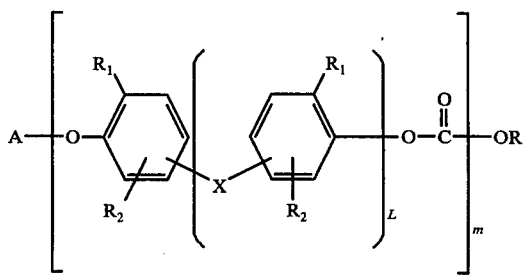

wherein independently at each occurrence $R_1$ denotes an alkyl, cycloalkyl or arylalkyl radical, $R_2$ denotes a hydrogen atom, or an alkyl, cycloalkyl or arylalkyl radical, A is a hydrogen atom or

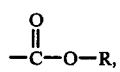

R is an alkyl or phenyl radical or

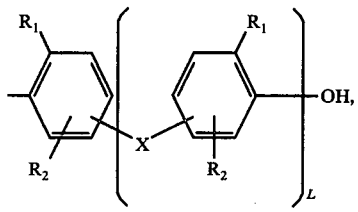

X is a direct bonding, -O-, -S-,

-CH₂SCH₂-, a divalent hydrocarbon radical or

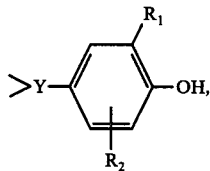

where Y is a trivalent hydrocarbon radical, B is selected from the group consisting of hydrogen and

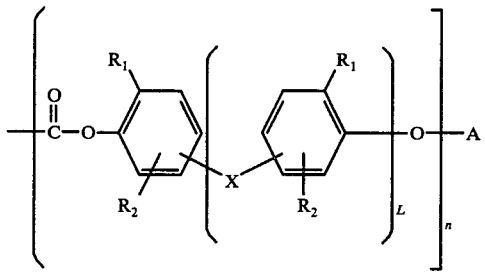

L is 0 or 1, $m$ is 1 to about 20, and $n$ is 0.1 to about 20.

2. A stabilizer composition according to claim 1 in which the weight ratio of the thioether ester to the carbonate ester is between 20 to 1 and 1 to 2.

3. A stabilizer composition according to claim 1 in which the thioether ester is an ester of 1,3,5-tris(2'hydroxyethylisocyanurate).

4. A stabilizer composition according to claim 1 in which the thioether ester is an ester of trimethylolethane.

5. A stabilizer composition according to claim 1 in which the thioether ester is an ester of trimethylolpropane.

6. A stabilizer composition according to claim 1 in which the thioether ester is an ester of pentaerythritol.

7. A stabilizer composition according to claim 1 in which the thioether ester is an ester of 3-n-dodecylthiopropionic acid.

8. A stabilizer composition according to claim 1 in which the thioether ester is an ester of a 3-alkylthio-2-methylpropionic acid.

9. A stabilizer composition according to claim 1 in which the carbonate ester is an ester of 2,5-di-t-butylhydroquinone.

10. A stabilizer composition in accordance with claim 1 in which the carbonate ester is an ester of an alkylidenebisphenol.

11. A stabilizer composition according to claim 1 in which the carbonate ester is an ester of bisphenol having two benzenoid rings linked through sulfur.

12. A stabilizer composition according to claim 1 in which the carbonate ester is an ester of trisphenol.

13. A stabilizer composition according to claim 1 containing as an additional stabilizing ingredient at least one compound selected from the group consisting of thiodipropionate esters, 1,2-epoxides, organic phosphites, and metal salts of monocarboxylic acids having 6 to 24 carbon atoms.

14. A stabilizer composition according to claim 1 in which the thioether ester has the formula

in which Z is a residue of a polyhydric alcohol, $R_3$ is selected from the group consisting of methyl and hydrogen, $R_4$ is a primary alkyl group having 1 to about 30 carbon atoms, p is an integer from 3 to 8, and q is an integer from zero to $p-1$.

15. A stabilized synthetic resin composition comprising a synthetic resin and a stabilizing amount of stabilizer composition according to claim 1.

16. A resin composition according to claim 15 in which the quantity of stabilizer composition is from 0.002 to 10 per cent by weight of the synthetic resin.

17. A resin composition according to claim 15 in which the resin is at least one polymer selected from the group consisting of olefin polymers, acrylic polymers, vinyl halide polymers, and polyamides.

18. A resin composition according to claim 16 in which the resin is an ethylene-vinyl acetate copolymer.

* * * * *